United States Patent
Szeto et al.

(10) Patent No.: US 9,895,410 B2
(45) Date of Patent: Feb. 20, 2018

(54) METHODS FOR PREVENTING AND TREATING ORAL CANCERS

(71) Applicant: Cornell University, Ithaca, NY (US)

(72) Inventors: Hazel Szeto, New York, NY (US); Lorraine Gudas, New York, NY (US); Xiaohan Tang, Staten Island, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/103,389

(22) PCT Filed: Dec. 11, 2014

(86) PCT No.: PCT/US2014/069815
§ 371 (c)(1),
(2) Date: Jun. 10, 2016

(87) PCT Pub. No.: WO2015/089316
PCT Pub. Date: Jun. 18, 2015

(65) Prior Publication Data
US 2017/0000840 A1   Jan. 5, 2017

Related U.S. Application Data

(60) Provisional application No. 61/915,310, filed on Dec. 12, 2013.

(51) Int. Cl.
| | |
|---|---|
| *A61K 38/06* | (2006.01) |
| *A61K 38/07* | (2006.01) |
| *C07K 5/08* | (2006.01) |
| *C07K 5/10* | (2006.01) |

(52) U.S. Cl.
CPC .............. *A61K 38/06* (2013.01); *A61K 38/07* (2013.01)

(58) Field of Classification Search
CPC .......... A61K 38/06; A61K 38/07; C07K 5/08; C07K 5/10
USPC ...................................................... 514/21.9
See application file for complete search history.

(56) References Cited

U.S. PATENT DOCUMENTS

| | | | |
|---|---|---|---|
| 6,387,700 B1 | 5/2002 | Rice et al. | |
| 8,592,373 B2 | 11/2013 | Szeto et al. | |
| 8,603,971 B2* | 12/2013 | Szeto ..................... | A61K 38/03 514/15.4 |
| 2009/0186832 A1 | 7/2009 | Franklin et al. | |
| 2010/0137208 A1 | 6/2010 | Varadhachary et al. | |
| 2010/0304395 A1 | 12/2010 | Ohto et al. | |
| 2013/0303436 A1* | 11/2013 | Wilson ..................... | C07K 7/00 514/1.9 |
| 2014/0349941 A1* | 11/2014 | Wilson ................... | A61K 38/04 514/15.4 |

OTHER PUBLICATIONS

Bihl, Michael P. et al., "Characterization of CDKN2A(p16) methylation and impact in colorectal cancer: systematic analysis using pyrosequencing," J of Translational Medicine, (2012), vol. 10, pp. 173, 10 pages.
Harris, R.E., "Cyclooxygenase-2 (cox-2) blockade in the chemoprevention of cancers of the colon, breast, prostate, and lung," Inflammopharmacology, (Apr. 2009), vol. 17, No. 2, pp. 55-67.
International Search Report and Written Opinion of the International Searching Authority for Application No. PCT/US2014/069815 dated Mar. 31, 2015, 12 pages.
Lou-Qian, Zhang et al., "The Prognostic Value of Epigenetic Silencing of p16 Gene in NSCLC Patients: A Systematic Review and Meta-Analysis," PLoS One, (Jan. 2013), vol. 8, Issue 1, e54970 (7 pages).
Osei-Sarfo, Kwame et al., "The molecular features of tongue epithelium treated with the carcinogen 4-nitroquinoline-1-oxide and alcohol as a model for HNSCC," Carcinogenesis, (2013), vol. 34, No. 11, pp. 2673-2681.
Shima, Kaori et al., "Prognostic significance of CDKN2A (p16) promoter methylation and loss of expression in 902 colorectal cancers: cohort study and literature review," Int. J. Cancer, (2011), vol. 128, pp. 1080-1094.
Tang, Xiao-Han et al., "A DNA Methyltransferase Inhibitor and All-trans Retinoic Acid Reduce Oral Cavity Carcinogenesis Induced by the Carcinogen 4-Nitroquinoline 1-Oxide," Cancer Prevention Research, (Dec. 2009), vol. 2, Issue 12, pp. 1100-1110.
Tang, Xiao-Han et al., "Oral Cavity and Esophageal Carcinogenesis Modeled in Carcinogen-Treated Mice," Clinical Cancer Research, (Jan. 1, 2004), vol. 10, pp. 301-313.
Tang, Xiao-Han et al., "Overexpression of lecithin:retinol acyltransferase in the epithelial basal layer makes mice more sensitive to oral cavity carcinogenesis induced by a carcinogen," Cancer Biology & Therapy, (Jul. 1, 2009), vol. 8, Issue 13, pp. 1214-1225.
Zhao, Kesheng et al., "Transcellular Transport of a Highly Polar 3+ Net Charge Opioid Tetrapeptide," Journal of Pharmacology and Experimental Therapeutics, (2003), vol. 304, No. 1, pp. 425-432.

* cited by examiner

*Primary Examiner* — Julie Ha
(74) *Attorney, Agent, or Firm* — Foley & Lardner LLP

(57) ABSTRACT

Methods for preventing or treating oral cancers, and/or reducing the severity of symptoms of oral cancers are described. The methods comprise administering an effective amount of an aromatic-cationic peptide to a subject in need thereof to normalize expression levels of genes involved in oral carcinogenesis.

12 Claims, 6 Drawing Sheets

METHODS FOR PREVENTING AND TREATING ORAL CANCERS

CROSS-REFERENCE TO RELATED APPLICATIONS

This application is a U.S. national phase application under 35 U.S.C. § 371 of International Application No. PCT/US2014/069815, filed on Dec. 11, 2014, which claims the benefit of and priority to U.S. Provisional Application No. 61/915,310 filed Dec. 12, 2013, the contents of which are incorporated herein by reference in their entireties.

GOVERNMENT SUPPORT

This invention was made with government support under grant number DER010389 awarded by the National Institutes of Health. The government has certain rights in the invention.

TECHNICAL FIELD

The present technology relates generally to methods for preventing or treating oral cancers, and/or reducing the severity of symptoms of oral cancers. In particular, the present technology relates to administering an effective amount of an aromatic-cationic peptide to a subject in need thereof to normalize expression levels of genes involved in oral carcinogenesis.

BACKGROUND

The following description is provided to assist the understanding of the reader. None of the information provided or references cited is admitted to be prior art to the present technology.

Oral squamous cell carcinoma (SCC) is one of the most common cancers in the world. Even though the cure rate for some small, primary tumors is high, many patients will develop secondary tumors and the long-term survival rate of this cancer is lower than 60%. Two major etiological factors in oral cavity SCC are tobacco and alcohol, and malignant transformation of the oral cavity tissue is thought to be related to exposure to certain carcinogens found in tobacco. Genetic instability caused by carcinogens leads to aneuploidy, and alterations in the expression and/or mutations in tumor suppressor genes, such as retinoic acid receptor β2 (RARβ2) and p53. In addition, carcinogens induce increased cell proliferation through the activation of additional genes, such as epidermal growth factor receptor (EGFR), cyclooxygenase 2 (Cox-2) or PTGS2, and cyclin D1.

SUMMARY

In one aspect, the disclosure provides a method of treating oral cancer in a subject in need thereof comprising administering to the subject a therapeutically effective amount of an aromatic-cationic peptide or a pharmaceutically acceptable salt thereof. In some embodiments of the method, the oral cancer is a squamous cell carcinoma.

In some embodiments of the method, the aromatic-cationic peptide is D-Arg-2',6'-Dmt-Lys-Phe-NH$_2$ or Phe-D-Arg-Phe-Lys-NH$_2$.

In some embodiments of the method, the pharmaceutically acceptable salt comprises acetate or trifluoroacetate salt.

In some embodiments of the method, the subject displays elevated levels of one or more of proliferating cell nuclear antigen (PCNA), p16, and PTGS2 compared to a healthy normal control. In some embodiments of the method, the subject is human.

In certain embodiments of the method, administration of the aromatic-cationic peptide results in a reduction in the number of oral tumors.

In some embodiments of the method, administration of the aromatic-cationic peptide results in a decrease in the severity of oral tumors.

Additionally or alternatively, in some embodiments of the method, the aromatic-cationic peptide is administered orally, topically, intranasally, systemically, locally intramuscularly, intravenously, subcutaneously, intracerebroventricularly, intrathecally, transdermally or with iontophoresis.

In some embodiments of the method, the subject is diagnosed as having oral cancer.

In some embodiments of the method, the oral cancer comprises one or more of leukoplakia (white lesions), erythroplakia, lumps or thickening in the oral soft tissues, soreness, difficulty chewing, speaking or swallowing, ear pain, difficulty moving the jaw or tongue, hoarseness, numbness of the tongue or other areas of the mouth, oral bleeding, wart-like masses, and swelling of the jaw that changes the way teeth or dentures fit together.

Additionally or alternatively, in some embodiments of the method, the aromatic-cationic peptide is administered at regular intervals over a period of one, two or several months. In certain embodiments of the method, the regular intervals are every day, every other day, every 3 days, every 4 days, every 5 days, every 6 days or once a week.

In another aspect, the present technology provides methods for normalizing the expression of one or more of proliferating cell nuclear antigen (PCNA), p16, and PTGS2 in a subject diagnosed with or susceptible to oral cancer comprising administering a therapeutically effective amount of an aromatic-cationic peptide or a pharmaceutically acceptable salt thereof.

In some embodiments of the method, the aromatic-cationic peptide is D-Arg-2',6'-Dmt-Lys-Phe-NH$_2$ or Phe-D-Arg-Phe-Lys-NH$_2$. In some embodiments of the method, the pharmaceutically acceptable salt comprises acetate or trifluoroacetate salt.

In certain embodiments of the method, administration of the aromatic-cationic peptide results in a reduction in the number of oral tumors.

In some embodiments of the method, administration of the aromatic-cationic peptide results in a decrease in the severity of oral tumors.

Additionally or alternatively, in some embodiments of the method, the aromatic-cationic peptide is administered orally, topically, intranasally, systemically, locally intramuscularly, intravenously, subcutaneously, intracerebroventricularly, intrathecally, transdermally or with iontophoresis.

In some embodiments of the method, the subject is diagnosed as having oral cancer.

In some embodiments of the method, the oral cancer comprises one or more of leukoplakia (white lesions), erythroplakia, lumps or thickening in the oral soft tissues, soreness, difficulty chewing, speaking or swallowing, ear pain, difficulty moving the jaw or tongue, hoarseness, numbness of the tongue or other areas of the mouth, oral bleeding, wart-like masses and swelling of the jaw that changes the way teeth or dentures fit together.

Additionally or alternatively, in some embodiments of the method, the aromatic-cationic peptide is administered at regular intervals over a period of one, two or several months. In certain embodiments of the method, the regular intervals are every day, every other day, every 3 days, every 4 days, every 5 days, every 6 days or once a week.

In some embodiments, the peptide is defined by formula I:

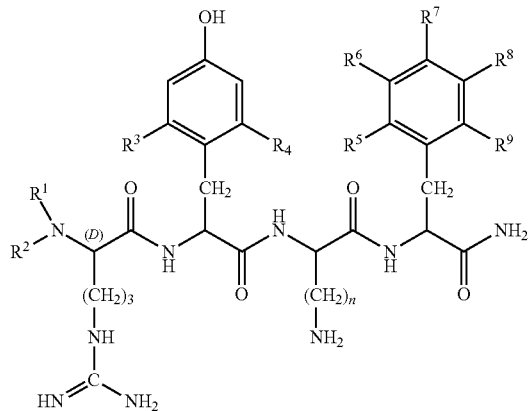

wherein $R^1$ and $R^2$ are each independently selected from
(i) hydrogen;
(ii) linear or branched $C_1$-$C_6$ alkyl;

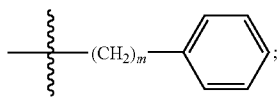

where $m$ = 1-3

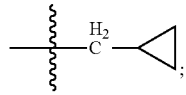

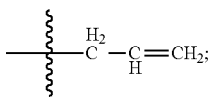

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;
$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In some embodiments, $R^1$ and $R^2$ are hydrogen; $R^3$ and $R^4$ are methyl; $R^5$, $R^6$, $R^7$, $R^8$, and $R^9$ are all hydrogen; and n is 4.

In some embodiments, the peptide is defined by formula II:

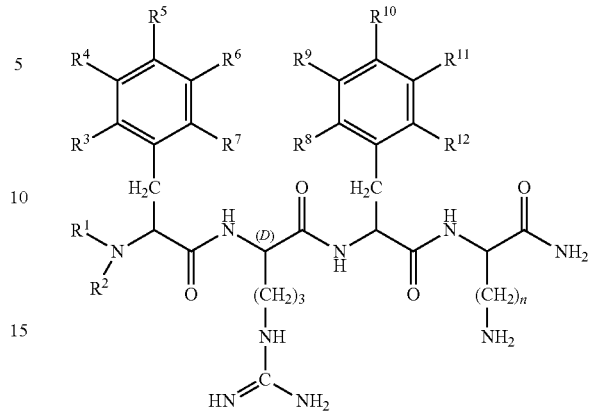

wherein $R^1$ and $R^2$ are each independently selected from
(i) hydrogen;
(ii) linear or branched $C_1$-$C_6$ alkyl;

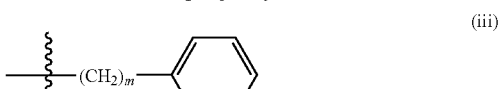

where m = 1-3;

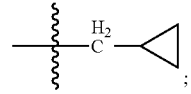

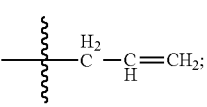

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In some embodiments, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

BRIEF DESCRIPTION OF THE DRAWINGS

FIG. 1A is a diagram of the experimental protocol. FIG. 1B shows the representative gross morphology of the mouse tongues and the gross tongue lesion grading system (10×).

FIG. 4A shows PCNA staining in tongue regions without visible lesions. FIG. 4B shows PCNA staining in tongue regions with visible lesions.

DETAILED DESCRIPTION

Figure 1A:
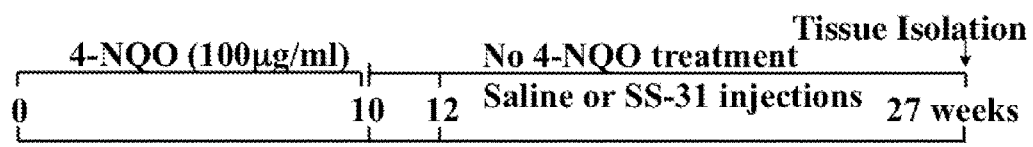
FIGS. 1A-B show carcinogenesis induced by the carcinogen 4-nitroquinoline 1-oxide (4-NQO) in mouse tongues. Wild type C57BL/6 mice (6 weeks old) were treated with propylene glycol (vehicle) or 4-NQO (100 μg/ml) in the drinking water for 10 weeks. Two weeks after the 4-NQO treatment was stopped, these 4-NQO treated mice were randomized (10 mice/group) to receive subcutaneous injections with either 100 μl saline or D-Arg-2',6'-Dmt-Lys-Phe-NH$_2$ two times/week for another 15 weeks before being sacrificed. The mice were then sacrificed, and the tongues were dissected out and photographed (10×). The grossly visible lesions on the whole tongues were graded in a double blinded manner.

It is to be appreciated that certain aspects, modes, embodiments, variations and features of the present technology are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which the present technology belongs.

All numerical designations, e.g., pH, temperature, time, concentration and molecular weight, including ranges, are approximations which are varied (+) or (−) by increments of 1.0 or 0.1, as appropriate, or alternatively by a variation of +/−10%, or alternatively 5% or alternatively 2%. Unless indicated otherwise, it is to be understood, although not always explicitly stated, that all numerical designations are preceded by the term "about".

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, a "control" is an alternative sample used in an experiment for comparison purpose. A control can be "positive" or "negative". For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the full or partial normalization of expression levels of genes involved in oral carcinogenesis in a subject in need thereof, or which results in partial or full amelioration of one or more symptoms of an oral cancer. In the context of therapeutic or prophylactic applications, in some embodiments, the amount of a composition administered to the subject will depend on the type and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, aromatic-cationic peptides, such as D-Arg-2',6'-Dmt-Lys-Phe-NH$_2$, or a pharmaceutically acceptable salt thereof, such as acetate or trifluoroacetate salt, may be administered to a subject having one or more signs, symptoms, or risk factors of oral cancer, including, but not limited to, leukoplakia (white lesions), erythroplakia, lumps or thickening in the oral soft tissues, soreness, difficulty chewing, speaking or swallowing, ear pain, difficulty moving the jaw or tongue, hoarseness, numbness of the tongue or other areas of the mouth, oral bleeding, wart-like masses and swelling of the jaw that changes the way teeth or dentures fit together. For example, a "therapeutically effective amount" of the aromatic-cationic peptides includes levels at which a the presence, frequency, or severity of one or more signs, symptoms, or risk factors of oral cancer are reduced or eliminated. In some embodiments, a therapeutically effective amount reduces or ameliorates the physiological effects of oral cancers, and/or the risk factors of oral cancers, and/or the likelihood of developing oral cancer.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound.

As used herein, "isolated" or "purified" polypeptide or peptide refers to a polypeptide or peptide that is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the terms "normalization" of, or to "normalize," the expression of a specific gene product is defined as changing the level of the gene product from a pathological value towards a normal value, where the normal value of the gene product can be 1) the level of the gene product in a healthy person or subject, or 2) a level of the gene product that alleviates one or more undesirable symptoms in the person or subject. That is, to normalize a gene product which is depressed in a disease state means to increase the level of the gene product towards the normal (healthy) value or towards a value which alleviates an undesirable symptom; to normalize a gene product which is elevated in a disease state means to decrease the level of the gene product towards the normal (healthy) value or towards a value which alleviates an undesirable symptom.

As used herein, the term "oral cancer" refers to cancers that form in tissues of the oral cavity (the mouth, including the lips, gums, tongue, inside lining of the cheeks, roof of the mouth and floor of the mouth) or the oropharynx (located behind the tonsils and the back of the throat). In some embodiments, the oral cancer originates from the flattened cells that make up the lining of the oral cavity, i.e., squamous cell carcinomas.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, "prevention" or "preventing" of a disease or condition refers to a compound that, in a statistical sample, reduces the occurrence of the disease or medical condition in the treated sample relative to an untreated control sample, or delays the onset of one or more symptoms of the disorder or condition relative to the untreated control sample. As used herein, preventing oral cancer includes preventing or delaying the initiation of oral cancer. As used herein, prevention of oral cancer also includes preventing a recurrence of one or more signs or symptoms of oral cancer.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, the term "subject" or "patient" includes both human and veterinary subjects, for example, humans, non-human primates, dogs, cats, sheep, mice, horses, and cows.

As used herein, the terms "treating" or "treatment" or "alleviation" or "amelioration" refers to the treatment of a disease or medical condition, in a subject, such as a human, and includes: (i) inhibiting a disease or medical condition, i.e., arresting its development; (ii) relieving a disease or medical condition, i.e., causing regression of the disease or medical condition; (iii) slowing progression of the disease or medical condition; and/or (iv) inhibiting, relieving, or slowing progression of one or more symptoms of the disease or medical condition.

Aromatic-Cationic Peptides

The aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. In some embodiments, the maximum number of amino acids is about twelve, about nine, about six, or about four.

The amino acids of the aromatic-cationic peptides can be any amino acid. As used herein, the term "amino acid" is used to refer to any organic molecule that contains at least one amino group and at least one carboxyl group. Typically, at least one amino group is at the a position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. Optimally, the peptide has no amino acids that are naturally occurring. The non-naturally occurring amino acids may be levorotary (L-), dextrorotary (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are suitably resistant or insensitive to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides may have less than five, less than four, less than three, or less than two contiguous L-amino acids recognized by common proteases, irrespective of whether the amino acids are naturally or non-naturally occurring. Optimally, the peptide has only D-amino acids, and no L-amino acids. In some embodiments, if the peptide contains protease sensitive sequences of amino acids, at least one of the amino acids is a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum numbers of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

Amino acid number and net positive charges ($3p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, a minimum of two net positive charges or a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

TABLE 4

Aromatic groups and net positive charges ($2a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:

TABLE 5

EXEMPLARY PEPTIDES

2',6'-Dmp-D-Arg-2',6'-Dmt-Lys-NH₂

2',6'-Dmp-D-Arg-Phe-Lys-NH₂

2',6'-Dmt-D-Arg-PheOrn-NH₂

2',6'-Dmt-D-Arg-Phe-Ahp (2-aminoheptanoicacid)-NH₂

2',6'-Dmt-D-Arg-Phe-Lys-NH₂

2',6'-Dmt-D-Cit-PheLys-NH₂

Ala-D-Phe-D-Arg-Tyr-Lys-D-Trp-His-D-Tyr-Gly-Phe

Arg-D-Leu-D-Tyr-Phe-Lys-Glu-D-Lys-Arg-D-Trp-Lys-

D-Phe-Tyr-D-Arg-Gly

Asp-Arg-D-Phe-Cys-Phe-D-Arg-D-Lys-Tyr-Arg-D-Tyr-

Trp-D-His-Tyr-D-Phe-Lys-Phe

Asp-D-Trp-Lys-Tyr-D-His-Phe-Arg-D-Gly-Lys-NH₂

D-Arg-2',6'-Dmt-Lys-Phe-NH₂

D-Glu-Asp-Lys-D-Arg-D-His-Phe-Phe-D-Val-Tyr-Arg-

Tyr-D-Tyr-Arg-His-Phe-NH₂

D-His-Glu-Lys-Tyr-D-Phe-Arg

D-His-Lys-Tyr-D-Phe-Glu-D-Asp-D-Asp-His-D-Lys-

Arg-Trp-NH₂

D-Tyr-Trp-Lys-NH₂

Glu-Arg-D-Lys-Tyr-D-Val-Phe-D-His-Trp-Arg-D-Gly-

Tyr-Arg-D-Met-NH₂

Gly-Ala-Lys-Phe-D-Lys-Glu-Arg-Tyr-His-D-Arg-D-

TABLE 5-continued

EXEMPLARY PEPTIDES

Arg-Asp-Tyr-Trp-D-His-Trp-His-D-Lys-Asp.

Gly-D-Phe-Lys-His-D-Arg-Tyr-NH₂

His-Tyr-D-Arg-Trp-Lys-Phe-D-Asp-Ala-Arg-Cys-D-

Tyr-His-Phe-D-Lys-Tyr-His-Ser-NH₂

Lys-D-Arg-Tyr-NH₂

Lys-D-Gln-Tyr-Arg-D-Phe-Trp-NH₂

Lys-Trp-D-Tyr-Arg-Asn-Phe-Tyr-D-His-NH₂

Met-Tyr-D-Arg-Phe-Arg-NH₂

Met-Tyr-D-Lys-Phe-Arg

Phe-Arg-D-His-Asp

Phe-D-Arg-2',6'-Dmt-Lys-NH₂

Phe-D-Arg-His

Phe-D-Arg-Lys-Trp-Tyr-D-Arg-His

Phe-D-Arg-Phe-Lys-NH₂

Phe-Phe-D-Tyr-Arg-Glu-Asp-D-Lys-Arg-D-Arg-His-

Phe-NH₂

Phe-Tyr-Lys-D-Arg-Trp-His-D-Lys-D-Lys-Glu-Arg-

D-Tyr-Thr

Thr-Gly-Tyr-Arg-D-His-Phe-Trp-D-His-Lys

Thr-Tyr-Arg-D-Lys-Trp-Tyr-Glu-Asp-D-Lys-D-Arg-

His-Phe-D-Tyr-Gly-Val-Ile-D-His-Arg-Tyr-Lys-NH₂

Trp-D-Lys-Tyr-Arg-NH₂

Trp-Lys-Phe-D-Asp-Arg-Tyr-D-His-Lys

Tyr-Asp-D-Lys-Tyr-Phe-D-Lys-D-Arg-Phe-Pro-D-Tyr-

His-Lys

Tyr-D-Arg-Phe-Lys-Glu-NH₂

Tyr-D-Arg-Phe-Lys-NH₂

Tyr-D-His-Phe-D-Arg-Asp-Lys-D-Arg-His-Trp-D-His-Phe

Tyr-His-D-Gly-Met

Val-D-Lys-His-Tyr-D-Phe-Ser-Tyr-Arg-NH₂

In one embodiment, the peptides have mu-opioid receptor agonist activity (i.e., they activate the mu-opioid receptor). Peptides, which have mu-opioid receptor agonist activity, are typically those peptides that have a tyrosine residue or a tyrosine derivative at the N-terminus (i.e., the first amino acid position). Suitable derivatives of tyrosine include 2'-methyltyrosine (Mmt); 2',6'-dimethyltyrosine (2'6'-Dmt); 3',5'-dimethyltyrosine (3'5'Dmt); N,2',6'-trimethyltyrosine (Tmt); and 2'-hydroxy-6'-methyltryosine (Hmt).

In one embodiment, a peptide that has mu-opioid receptor agonist activity has the formula Tyr-D-Arg-Phe-Lys-NH₂. Tyr-D-Arg-Phe-Lys-NH₂ has a net positive charge of three, contributed by the amino acids tyrosine, arginine, and lysine and has two aromatic groups contributed by the amino acids phenylalanine and tyrosine. The tyrosine of Tyr-D-Arg-Phe- Lys-NH$_2$ can be a modified derivative of tyrosine such as in 2',6'-dimethyltyrosine to produce the compound having the formula 2',6'-Dmt-D-Arg-Phe-Lys-NH$_2$. 2',6'-Dmt-D-Arg-Phe-Lys-NH$_2$ has a molecular weight of 640 and carries a net three positive charge at physiological pH. 2',6'-Dmt-D-Arg-Phe-Lys-NH$_2$ readily penetrates the plasma membrane of several mammalian cell types in an energy-independent manner (Zhao et al., *J. Pharmacol Exp Ther.*, 304:425-432, 2003).

Alternatively, in other instances, the aromatic-cationic peptide does not have mu-opioid receptor agonist activity. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment. Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-NH$_2$. Alternatively, the N-terminal phenylalanine can be a derivative of phenylalanine such as 2',6'-dimethylphenylalanine (2'6'-Dmp). Tyr-D-Arg-Phe-Lys-NH$_2$ containing 2',6'-dimethylphenylalanine at amino acid position 1 has the formula 2',6'-Dmp-D-Arg-Phe-Lys-NH$_2$. In one embodiment, the amino acid sequence of 2',6'-Dmt-D-Arg-Phe-Lys-NH$_2$ is rearranged such that Dmt is not at the N-terminus. An example of such an aromatic-cationic peptide that does not have mu-opioid receptor agonist activity has the formula D-Arg-2',6'-Dmt-Lys-Phe-NH$_2$.

Suitable substitution variants of the peptides listed herein include conservative amino acid substitutions. Amino acids may be grouped according to their physicochemical characteristics as follows:

(a) Non-polar amino acids: Ala(A) Ser(S) Thr(T) Pro(P) Gly(G) Cys (C);

(b) Acidic amino acids: Asn(N) Asp(D) Glu(E) Gln(Q);

(c) Basic amino acids: His(H) Arg(R) Lys(K);

(d) Hydrophobic amino acids: Met(M) Leu(L) Ile(I) Val (V); and (e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group are generally more likely to alter the characteristics of the original peptide.

Examples of peptides that activate mu-opioid receptors include, but are not limited to, the aromatic-cationic peptides shown in Table 6.

TABLE 6

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | NH$_2$ |
| Tyr | D-Arg | Phe | Orn | NH$_2$ |
| Tyr | D-Arg | Phe | Dab | NH$_2$ |
| Tyr | D-Arg | Phe | Dap | NH$_2$ |
| 2',6'Dmt | D-Arg | Phe | Lys | NH$_2$ |
| 2',6'Dmt | D-Arg | Phe | Lys-NH(CH$_2$)$_2$—NH-dns | NH$_2$ |
| 2',6'Dmt | D-Arg | Phe | Lys-NH(CH$_2$)$_2$—NH-atn | NH$_2$ |
| 2',6'Dmt | D-Arg | Phe | dnsLys | NH$_2$ |
| 2',6'Dmt | D-Cit | Phe | Lys | NH$_2$ |
| 2',6'Dmt | D-Cit | Phe | Ahp | NH$_2$ |
| 2',6'Dmt | D-Arg | Phe | Orn | NH$_2$ |
| 2',6'Dmt | D-Arg | Phe | Dab | NH$_2$ |
| 2',6'Dmt | D-Arg | Phe | Dap | NH$_2$ |
| 2',6'Dmt | D-Arg | Phe | Ahp(2-aminoheptanoic acid) | NH$_2$ |
| Bio-2',6'Dmt | D-Arg | Phe | Lys | NH$_2$ |
| 3',5'Dmt | D-Arg | Phe | Lys | NH$_2$ |
| 3',5'Dmt | D-Arg | Phe | Orn | NH$_2$ |
| 3',5'Dmt | D-Arg | Phe | Dab | NH$_2$ |
| 3',5'Dmt | D-Arg | Phe | Dap | NH$_2$ |
| Tyr | D-Arg | Tyr | Lys | NH$_2$ |
| Tyr | D-Arg | Tyr | Orn | NH$_2$ |
| Tyr | D-Arg | Tyr | Dab | NH$_2$ |
| Tyr | D-Arg | Tyr | Dap | NH$_2$ |
| 2',6'Dmt | D-Arg | Tyr | Lys | NH$_2$ |
| 2',6'Dmt | D-Arg | Tyr | Orn | NH$_2$ |
| 2',6'Dmt | D-Arg | Tyr | Dab | NH$_2$ |
| 2',6'Dmt | D-Arg | Tyr | Dap | NH$_2$ |
| 2',6'Dmt | D-Arg | 2'6'Dmt | Lys | NH$_2$ |
| 2',6'Dmt | D-Arg | 2'6'Dmt | Orn | NH$_2$ |
| 2',6'Dmt | D-Arg | 2'6'Dmt | Dab | NH$_2$ |
| 2',6'Dmt | D-Arg | 2'6'Dmt | Dap | NH$_2$ |
| 3',5'Dmt | D-Arg | 3'5'Dmt | Arg | NH$_2$ |
| 3',5'Dmt | D-Arg | 3'5'Dmt | Lys | NH$_2$ |
| 3',5'Dmt | D-Arg | 3'5'Dmt | Orn | NH$_2$ |
| 3',5'Dmt | D-Arg | 3'5'Dmt | Dab | NH$_2$ |
| Tyr | D-Lys | Phe | Dap | NH$_2$ |
| Tyr | D-Lys | Phe | Arg | NH$_2$ |
| Tyr | D-Lys | Phe | Lys | NH$_2$ |
| Tyr | D-Lys | Phe | Orn | NH$_2$ |
| 2',6'Dmt | D-Lys | Phe | Dab | NH$_2$ |
| 2',6'Dmt | D-Lys | Phe | Dap | NH$_2$ |
| 2',6'Dmt | D-Lys | Phe | Arg | NH$_2$ |
| 2',6'Dmt | D-Lys | Phe | Lys | NH$_2$ |
| 3',5'Dmt | D-Lys | Phe | Orn | NH$_2$ |
| 3',5'Dmt | D-Lys | Phe | Dab | NH$_2$ |
| 3',5'Dmt | D-Lys | Phe | Dap | NH$_2$ |
| 3',5'Dmt | D-Lys | Phe | Arg | NH$_2$ |
| Tyr | D-Lys | Tyr | Lys | NH$_2$ |
| Tyr | D-Lys | Tyr | Orn | NH$_2$ |
| Tyr | D-Lys | Tyr | Dab | NH$_2$ |
| Tyr | D-Lys | Tyr | Dap | NH$_2$ |
| 2',6'Dmt | D-Lys | Tyr | Lys | NH$_2$ |
| 2',6'Dmt | D-Lys | Tyr | Orn | NH$_2$ |
| 2',6'Dmt | D-Lys | Tyr | Dab | NH$_2$ |
| 2',6'Dmt | D-Lys | Tyr | Dap | NH$_2$ |
| 2',6'Dmt | D-Lys | 2'6'Dmt | Lys | NH$_2$ |
| 2',6'Dmt | D-Lys | 2'6'Dmt | Orn | NH$_2$ |
| 2',6'Dmt | D-Lys | 2'6'Dmt | Dab | NH$_2$ |
| 2',6'Dmt | D-Lys | 2'6'Dmt | Dap | NH$_2$ |
| 2',6'Dmt | D-Arg | Phe | dnsDap | NH$_2$ |
| 2',6'Dmt | D-Arg | Phe | atnDap | NH$_2$ |
| 3',5'Dmt | D-Lys | 3'5'Dmt | Lys | NH$_2$ |
| 3',5'Dmt | D-Lys | 3'5'Dmt | Orn | NH$_2$ |
| 3',5'Dmt | D-Lys | 3'5'Dmt | Dab | NH$_2$ |
| 3',5'Dmt | D-Lys | 3'5'Dmt | Dap | NH$_2$ |
| Tyr | D-Lys | Phe | Arg | NH$_2$ |
| Tyr | D-Orn | Phe | Arg | NH$_2$ |
| Tyr | D-Dab | Phe | Arg | NH$_2$ |
| Tyr | D-Dap | Phe | Arg | NH$_2$ |
| 2',6'Dmt | D-Arg | Phe | Arg | NH$_2$ |

TABLE 6-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| 2',6'Dmt | D-Lys | Phe | Arg | $NH_2$ |
| 2',6'Dmt | D-Orn | Phe | Arg | $NH_2$ |
| 2',6'Dmt | D-Dab | Phe | Arg | $NH_2$ |
| 3',5'Dmt | D-Dap | Phe | Arg | $NH_2$ |
| 3',5'Dmt | D-Arg | Phe | Arg | $NH_2$ |
| 3',5'Dmt | D-Lys | Phe | Arg | $NH_2$ |
| 3',5'Dmt | D-Orn | Phe | Arg | $NH_2$ |
| Tyr | D-Lys | Tyr | Arg | $NH_2$ |
| Tyr | D-Orn | Tyr | Arg | $NH_2$ |
| Tyr | D-Dab | Tyr | Arg | $NH_2$ |
| Tyr | D-Dap | Tyr | Arg | $NH_2$ |
| 2',6'Dmt | D-Arg | 2'6'Dmt | Arg | $NH_2$ |
| 2',6'Dmt | D-Lys | 2'6'Dmt | Arg | $NH_2$ |
| 2',6'Dmt | D-Orn | 2'6'Dmt | Arg | $NH_2$ |
| 2',6'Dmt | D-Dab | 2'6'Dmt | Arg | $NH_2$ |
| 3',5'Dmt | D-Dap | 3'5'Dmt | Arg | $NH_2$ |
| 3',5'Dmt | D-Arg | 3'5'Dmt | Arg | $NH_2$ |
| 3',5'Dmt | D-Lys | 3'5'Dmt | Arg | $NH_2$ |
| 3',5'Dmt | D-Orn | 3'5'Dmt | Arg | $NH_2$ |
| Mmt | D-Arg | Phe | Lys | $NH_2$ |
| Mmt | D-Arg | Phe | Orn | $NH_2$ |
| Mmt | D-Arg | Phe | Dab | $NH_2$ |
| Mmt | D-Arg | Phe | Dap | $NH_2$ |
| Tmt | D-Arg | Phe | Lys | $NH_2$ |
| Tmt | D-Arg | Phe | Orn | $NH_2$ |
| Tmt | D-Arg | Phe | Dab | $NH_2$ |
| Tmt | D-Arg | Phe | Dap | $NH_2$ |
| Hmt | D-Arg | Phe | Lys | $NH_2$ |
| Hmt | D-Arg | Phe | Orn | $NH_2$ |
| Hmt | D-Arg | Phe | Dab | $NH_2$ |
| Hmt | D-Arg | Phe | Dap | $NH_2$ |
| Mmt | D-Lys | Phe | Lys | $NH_2$ |
| Mmt | D-Lys | Phe | Orn | $NH_2$ |
| Mmt | D-Lys | Phe | Dab | $NH_2$ |
| Mmt | D-Lys | Phe | Dap | $NH_2$ |
| Mmt | D-Lys | Phe | Arg | $NH_2$ |
| Tmt | D-Lys | Phe | Lys | $NH_2$ |
| Tmt | D-Lys | Phe | Orn | $NH_2$ |
| Tmt | D-Lys | Phe | Dab | $NH_2$ |
| Tmt | D-Lys | Phe | Dap | $NH_2$ |
| Tmt | D-Lys | Phe | Arg | $NH_2$ |
| Hmt | D-Lys | Phe | Lys | $NH_2$ |
| Hmt | D-Lys | Phe | Orn | $NH_2$ |
| Hmt | D-Lys | Phe | Dab | $NH_2$ |
| Hmt | D-Lys | Phe | Dap | $NH_2$ |
| Hmt | D-Lys | Phe | Arg | $NH_2$ |
| Mmt | D-Lys | Phe | Arg | $NH_2$ |
| Mmt | D-Orn | Phe | Arg | $NH_2$ |
| Mmt | D-Dab | Phe | Arg | $NH_2$ |
| Mmt | D-Dap | Phe | Arg | $NH_2$ |
| Mmt | D-Arg | Phe | Arg | $NH_2$ |
| Tmt | D-Lys | Phe | Arg | $NH_2$ |
| Tmt | D-Orn | Phe | Arg | $NH_2$ |
| Tmt | D-Dab | Phe | Arg | $NH_2$ |
| Tmt | D-Dap | Phe | Arg | $NH_2$ |
| Tmt | D-Arg | Phe | Arg | $NH_2$ |
| Hmt | D-Lys | Phe | Arg | $NH_2$ |
| Hmt | D-Orn | Phe | Arg | $NH_2$ |
| Hmt | D-Dab | Phe | Arg | $NH_2$ |
| Hmt | D-Dap | Phe | Arg | $NH_2$ |
| Hmt | D-Arg | Phe | Arg | $NH_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of peptides that do not activate mu-opioid receptors include, but are not limited to, the aromatic-cationic peptides shown in Table 7.

TABLE 7

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Phe | Lys | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexyl alanine

The amino acids of the peptides shown in Table 6 and 7 may be in either the L- or the D-configuration.

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.*, 289, Academic Press, Inc., New York (1997).

Oral Cancers

Oral cancers comprise about 85% of a group of cancers commonly referred to as head and neck cancers. Other oral cancers include basal cell carcinoma, fibromas, osteomas, malignant tumors of connective tissue origin, tumors of the teeth and salivary gland tumors.

The death rate associated with oral cancer is particularly high not because it is hard to discover or diagnose, but due to the cancer being routinely discovered late in its development. Another obstacle to early discovery (and resulting better outcomes) is the advent of a virus, HPV 16, contributing more to the incidence rate of oral cancers, particularly in the posterior part of the mouth (the oropharynx, the tonsils, the base of tongue areas) which many times does not produce visible lesions or discolorations that have historically been the early warning signs of the disease process.

Often oral cancer is only discovered when the cancer has metastasized to another location, most likely the lymph nodes of the neck. Prognosis at this stage of discovery is significantly worse than when it is caught in a localized intra oral area. Besides the metastasis, at these later stages, the primary tumor has had time to invade deep into local structures.

Oral cancer is particularly dangerous because in its early stages it may not be noticed by the patient, as it can frequently prosper without producing pain or symptoms they might readily recognize, and because it has a high risk of producing second, primary tumors. This means that patients who survive a first encounter with the disease, have up to a 20 times higher risk of developing a second cancer. This heightened risk factor can last for 5 to 10 years after the first occurrence. There are several types of oral cancers, but around 90% are squamous cell carcinomas. It is estimated that approximately $3.2 billion is spent in the United States each year on treatment of head and neck cancers.

Clinical Manifestations

One of the real dangers of oral cancers is that it can go unnoticed in its early stages. Oral cancers may appear as a white or red patch of tissue in the mouth, or a small indurated ulcer which looks like a common canker sore. Other symptoms include; a lump or mass which can be felt inside the mouth or neck, pain or difficulty in swallowing, speaking, or chewing, any wart-like masses, hoarseness which lasts for a long time, or any numbness in the oral/facial region. Unilateral persistent ear ache can also be a warning sign. Oral cancers can spread into the jaw.

Other than the lips, common areas for oral cancer to develop in the anterior of the mouth are on the tongue and the floor of the mouth. Individuals that use chewing tobacco, are likely to have them develop in the sulcus between the lip or cheek and the soft tissue (gingiva) covering the lower jaw (mandible) where the plug of tobacco is held repeatedly. There are also a small number of cancers that are unique to the salivary glands. While the occurrence of these specific cancer types is dwarfed by the other oral cancers, they are a small percentage of the total incidence rate.

In the US, cancers of the hard palate are uncommon, though not unknown. The base of the tongue at the back of the mouth, the oropharynx (the back of the throat) and on the pillars of the tonsils, and the tonsillar crypt and the tonsil itself, are other sites where oral cancers are commonly found, particularly in young non-smoking individuals.

Risk Factors

Age is frequently named as a risk factor for oral cancer, as historically it occurs in those over the age of 40. Other risk factors include tobacco use, alcohol consumption, vitamin A and iron deficiency, exposure to ultraviolet radiation or X-rays, and persistent viral infections such as HPV. Subjects who both smoke and drink, have a 15 times greater risk of developing oral cancer than others.

Biological risk factors include viruses and fungi, which have been found in association with oral cancers. The human papilloma virus, particularly HPV16, has been definitively implicated in oral cancers, particularly those that occur in the back of the mouth (oropharynx, base of tongue, tonsillar pillars and crypt, as well as the tonsils themselves). HPV is a common, sexually transmitted virus, which infects about 40 million Americans today. There are about 200 strains of HPV, the majority of which are thought to be harmless. Genetic predisposition may also lead to the development of oral squamous cell carcinomas, e.g., genetic mutations in cell cycle regulators.

Diagnosis

Oral cancers are typically diagnosed via tissue biopsy. The following stages are used to describe oral cancers:

Stage I: The cancer is less than 2 centimeters in size (about 1 inch), and has not spread to lymph nodes in the area.

Stage II: The cancer is more than 2 centimeters in size, but less than 4 centimeters (less than 2 inches), and has not spread to lymph nodes in the area.

Stage III: The cancer is either more than 4 centimeters in size or is any size but has spread to only one lymph node on the same side of the neck as the cancer. The lymph node that contains cancer measures no more than 3 centimeters.

Stage IV: The cancer has spread to tissues around the lip and oral cavity. The lymph nodes in the area may or may not contain cancer. The cancer is any size and has spread to more than one lymph node on the same side of the neck as the cancer, to lymph nodes on one or both sides of the neck, or to any lymph node that measures more than 6 centimeters (over 2 inches). The cancer has spread to other parts of the body.

Recurrent: means that the cancer has recurred in the lip and oral cavity or in another part of the body after it has been treated.

Another method of staging oral carcinomas is referred to as the TNM method. In this method T describes the tumor, N describes the lymph nodes, and M describes distant metastasis.

Current Treatment Options

The actual curative treatment modalities for oral cancers are usually chemotherapy with concurrent radiation, sometimes combined with surgery. Each of these modalities is associated with side effects. Chemotherapy while able to kill cancer cells itself is currently not used as a monotherapy for oral cancers. Chemotherapy decreases the possibility of metastasis, sensitizes the malignant cells to radiation, reduces the size of any malignancy prior to surgery, or and is used in patients who have confirmed distant metastasis of the disease. Whether a patient has surgery, radiation and surgery, or radiation, surgery, and chemotherapy, is dependent on the stage of development of the cancer.

Therapeutic Methods

The following discussion is presented by way of example only, and is not intended to be limiting.

One aspect of the present technology includes methods of treating oral cancers in a subject diagnosed as having, suspected as having, or at risk of having oral cancer. In therapeutic applications, compositions or medicaments comprising an aromatic-cationic peptide, such as D-Arg-2', 6'-Dmt-Lys-Phe-NH$_2$, or a pharmaceutically acceptable salt thereof, such as acetate or trifluoroacetate salt, are administered to a subject suspected of, or already suffering from such a disease, such as, e.g., aberrant levels and/or function of genes involved in oral carcinogenesis compared to a normal control subject, or oral cancer, in an amount sufficient to cure, or at least partially arrest, the symptoms of the disease, including its complications and intermediate pathological phenotypes in development of the disease.

Subjects suffering from oral cancer can be identified by any or a combination of diagnostic or prognostic assays known in the art. For example, typical symptoms of oral cancer include, but are not limited to, leukoplakia (white lesions), erythroplakia, lumps or thickening in the oral soft tissues, soreness, difficulty chewing, speaking or swallowing, ear pain, difficulty moving the jaw or tongue, hoarseness, numbness of the tongue or other areas of the mouth, oral bleeding, wart-like masses and swelling of the jaw that changes the way teeth or dentures fit together.

In some embodiments, the subject may exhibit aberrant levels or function of genes involved in oral carcinogenesis compared to a normal control subject, which are measureable using techniques known in the art.

In some embodiments, oral cancer subjects treated with the aromatic-cationic peptide will show amelioration or elimination of one or more of the following symptoms: leukoplakia (white lesions), erythroplakia, lumps or thickening in the oral soft tissues, soreness, difficulty chewing, speaking or swallowing, ear pain, difficulty moving the jaw or tongue, hoarseness, numbness of the tongue or other areas of the mouth, oral bleeding, wart-like masses and swelling of the jaw that changes the way teeth or dentures fit together. In some embodiments, oral cancer subjects treated with the aromatic-cationic peptide will show decreased levels of PCNA or PTGS2 and/or increased levels of p16.

Prophylactic Methods

In one aspect, the present technology provides a method for preventing or delaying the onset of oral cancer or symptoms of oral cancer in a subject at risk of having oral cancer. In some embodiments, the subject may exhibit one or more mutations in genes involved in oral carcinogenesis.

Subjects at risk for aberrant levels and/or function of genes involved in oral carcinogenesis compared to a normal control subject or oral cancer can be identified by, e.g., any or a combination of diagnostic or prognostic assays known in the art. In prophylactic applications, pharmaceutical compositions or medicaments of aromatic-cationic peptides, such as D-Arg-2',6'-Dmt-Lys-Phe-NH$_2$, or a pharmaceutically acceptable salt thereof, such as acetate or trifluoroacetate salt, are administered to a subject susceptible to, or otherwise at risk of a disease or condition such as e.g., oral cancer, in an amount sufficient to eliminate or reduce the risk, or delay the outset of the disease, including biochemical, histologic and/or behavioral symptoms of the disease, its complications and intermediate pathological phenotypes presenting during development of the disease. Administration of a prophylactic aromatic-cationic peptide can occur prior to the manifestation of symptoms characteristic of the disease or disorder, such that the disease or disorder is prevented or, alternatively, delayed in its onset.

Subjects or at risk for aberrant levels and/or function of genes involved oral carcinogenesis compared to a normal control subject or oral cancer include, but are not limited to, subjects harboring mutations in one or more genes involved in oral carcinogenesis.

In some embodiments, treatment with the aromatic-cationic peptide will prevent or delay the onset of one or more of the following symptoms: leukoplakia (white lesions), erythroplakia, lumps or thickening in the oral soft tissues, soreness, difficulty chewing, speaking or swallowing, ear pain, difficulty moving the jaw or tongue, hoarseness, numbness of the tongue or other areas of the mouth, oral bleeding, wart-like masses and swelling of the jaw that changes the way teeth or dentures fit together. In some embodiments, oral cancers subjects treated with the aromatic-cationic peptide will show will show normal levels of PCNA, p16 and/or PTGS2.

For therapeutic and/or prophylactic applications, a composition comprising an aromatic-cationic peptide, such as D-Arg-2',6'-Dmt-Lys-Phe-NH$_2$, or a pharmaceutically acceptable salt thereof, such as acetate or trifluoroacetate salt, is administered to the subject. In some embodiments, the peptide composition is administered one, two, three, four, or five times per day. In some embodiments, the peptide composition is administered more than five times per day. Additionally or alternatively, in some embodiments, the peptide composition is administered every day, every other day, every third day, every fourth day, every fifth day, or every sixth day. In some embodiments, the peptide composition is administered weekly, bi-weekly, tri-weekly, or monthly. In some embodiments, the peptide composition is administered for a period of one, two, three, four, or five weeks. In some embodiments, the peptide is administered for six weeks or more. In some embodiments, the peptide is administered for twelve weeks or more. In some embodiments, the peptide is administered for a period of less than one year. In some embodiments, the peptide is administered for a period of more than one year.

Determination of the Biological Effect of the Aromatic-Cationic Peptide-Based Therapeutic In various embodiments, suitable in vitro or in vivo assays are performed to determine the effect of a specific aromatic-cationic peptide-based therapeutic and whether its administration is indicated for treatment. In various embodiments, in vitro assays can be performed with representative animal models, to determine if a given aromatic-cationic peptide-based therapeutic exerts the desired effect on reducing or eliminating signs and/or symptoms of oral cancer. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. In some embodiments, in vitro or in vivo testing is directed to the biological function of D-Arg-2',6'-Dmt-Lys-Phe-NH$_2$, or a pharmaceutically acceptable salt thereof, such as acetate or trifluoroacetate salt.

Animal models of oral cancer may be generated using techniques known in the art. For example, a murine model of oral squamous cell carcinoma can be generated by exposing animals to the carcinogen 4-NQO via drinking water, as disclosed herein. Such models may be used to demonstrate the biological effect of aromatic-cationic peptides of the present technology, such as D-Arg-2',6'-Dmt-Lys-Phe-NH$_2$, in the prevention and treatment of conditions arising from disruption of a particular gene, and for determining what comprises a therapeutically effective amount of peptide in a given context.

Modes of Administration and Effective Dosages

The peptide useful in the methods of the present technology is administered to a mammal in an amount effective in treating or preventing oral cancers. The effective amount is determined during pre-clinical trials and clinical trials by methods familiar to physicians and clinicians.

An effective amount of a peptide useful in the methods of the present technology, for example in a pharmaceutical composition, may be administered to a mammal in need thereof by any of a number of well-known methods for administering pharmaceutical compounds.

The peptide may be administered systemically or locally. In one embodiment, the peptide is administered intravenously. For example, the aromatic-cationic peptides useful in the methods of the present technology may be administered via rapid intravenous bolus injection. In some embodiments, the peptide is administered as a constant rate intravenous infusion.

The peptide may also be administered orally, topically, intranasally, intramuscularly, subcutaneously, or transdermally. In one particular embodiment, transdermal administration of the aromatic-cationic peptides is by iontophoresis, in which the charged peptide is delivered across the skin by an electric current.

Other routes of administration include intracerebroventricularly or intrathecally. Intracerebroventiculatly refers to administration into the ventricular system of the brain.

Intrathecally refers to administration into the space under the arachnoid membrane of the spinal cord.

The peptides useful in the methods of the present technology may also be administered to mammals by sustained release, as is known in the art. Sustained release administration is a method of drug delivery to achieve a certain level of the drug over a particular period of time. The level typically is measured by serum or plasma concentration.

Any formulation known in the art of pharmacy is suitable for administration of the aromatic-cationic peptides useful in the methods of the present technology. For oral administration, liquid or solid formulations may be used. Some examples of formulations include tablets, gelatin capsules, pills, troches, elixirs, suspensions, syrups, wafers, chewing gum and the like. The peptides can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the aromatic-cationic peptides useful in the methods of the present technology may utilize conventional diluents, carriers, or excipients etc., such as are known in the art can be employed to deliver the peptides. For example, the formulations may comprise one or more of the following: a stabilizer, a surfactant, such as a nonionic surfactant, and optionally a salt and/or a buffering agent. The peptide may be delivered in the form of an aqueous solution, or in a lyophilized form.

In some embodiments, the stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. In some embodiments, the stabilizer or combination of stabilizers constitutes from about 0.1% to about 10% weight for weight of the peptide.

In some embodiments, the surfactant is a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. In certain embodiments, the buffering agent maintains the pH of the pharmaceutical composition in the range of about 5.5 to about 7.5. The salt and/or buffering agent is also useful to maintain the osmolality at a level suitable for administration to a human or an animal. In some embodiments, the salt or buffering agent is present at a roughly isotonic concentration of about 150 mM to about 300 mM.

The formulations of the peptides useful in the methods of the present technology may additionally contain one or more conventional additives. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., as described above. As a further precaution against oxidation or other spoilage, the pharmaceutical compositions may be stored under nitrogen gas in vials sealed with impermeable stoppers.

The mammal can be any mammal, including, for example, farm animals, such as sheep, pigs, cows, and horses; pet animals, such as dogs and cats; laboratory animals, such as rats, mice and rabbits. In one embodiment, the mammal is a human.

Combination Therapy with Aromatic-Cationic Peptides

In some embodiments, the aromatic-cationic peptides, such as D-Arg-2',6'-Dmt-Lys-Phe-NH$_2$, or a pharmaceutically acceptable salt thereof, such as acetate or trifluoroacetate salt, may be combined with one or more additional therapies for the prevention or treatment of oral cancer. Additional therapeutic agents or active agents include, but are not limited to, alkylating agents, nitrosoureas, antimetabolites, antitumor antibiotics, plant vinca alkaloids, and steroid hormones.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

EXAMPLES

The present technology is further illustrated by the following examples, which should not be construed as limiting in any way.

Example 1. General Methods Used to Study Oral Carcinogenesis in a Mouse Model

A mouse model of oral squamous cell carcinomas or oral cancers was developed by exposing the animals to the carcinogen 4-nitroquinoline 1-oxide (4-NQO) via drinking water. This in vivo mouse model shows similarities to human oral tumors in terms of their morphological, histopathological, and molecular characteristics.

Six-week old wild-type C57BL/6 female mice (purchased from the Jackson Laboratory) were used for this study. The mice were maintained on a normal chow (Lab-diet with constant nutrition, Lab-Diet Co, St. Louis, Mo.) and under controlled conditions with a 12 hour light/dark cycle. The mice were randomly divided into an experimental group in which mice received drinking water that contained 100 μg/ml 4-nitroquinoline 1-oxide (4-NQO) (Sigma, St. Louis, Mo.) and a control group in which mice received drinking water that contained propylene glycol (vehicle for 4-NQO). The treatment lasted for 10 weeks after which the mice received regular drinking water. Two weeks after the termination of the 4-NQO treatment, all mice were divided into 3 groups (10 mice/group): A) control mice, no further treatments; B) 4-NQO treated mice, subcutaneous injection of 0.1 ml saline; C) 4-NQO treated mice, subcutaneous injection of 0.1 ml D-Arg-2',6'-Dmt-Lys-Phe-NH$_2$ (dissolved in saline, 2.5 mg/kg/day) on 2 days each week (Tuesdays and Fridays). The treatments lasted for 15 weeks. Mouse body weights and precancerous and cancerous lesions were monitored in the oral cavities at different times for up to 15 weeks, or until signs of sickness or weight loss. All experiments were performed under a WCMC IACUC approved protocol.

Tissue dissection, lesion grade measurement, and pathological diagnosis. Tongues of mice were dissected immediately after cervical dislocation. Gross lesions were identified and photographed, and visible cancerous lesions on the tongues were counted. The multiplicity of lesions (number of lesions per mouse) was assessed with a 10× magnification. The severity of gross lesions on the tongues was quantified by a grading system that included 0 (no lesion), 1 (mild lesion), 2 (intermediate lesion), 3 (severe lesion), and 4 (most severe lesion) in a double blinded manner. Mouse tongues were fixed in freshly made 4% paraformaldehyde overnight at 4° C., embedded in paraffin, and sectioned into 5 μm sections. The histological diagnosis of squamous neoplasia (four representative mice per group, based on the lesion grades) was performed by a pathologist on the hematoxylin and eosin (H & E) stained, sectioned tissue samples. The lesions observed were classified into three types: epithelial hyperplasia, dysplasia (mild, moderate, and severe), and squamous cell carcinoma (SCC), as described previously in Tang et al., *Clin Cancer Res.*, 10(1):301-13 (2004) and Tang et al., *Cancer Biology & Therapy*, 8(13): 1212-1213 (2009).

Immunohistochemistry. Paraffin embedded sections (from four mice per group) were deparaffinized, rehydrated, and antigen retrieval was performed. The tissue sections were stained by using the M.O.M. kit (for the p16 Ab) (Vector Laboratories, Burlingame, Calif.), the Envision™+HRP (DAB+) kit (for the proliferating cell nuclear antigen (PCNA) Ab) (Dako, Carpinteria, Calif.), or the Invitrogen Superpicture kit (for the Cox-2 Ab) (Invitrogen, South San Francisco, Calif.). After quenching endogenous peroxidase with 3% $H_2O_2$, the tissue sections were blocked with blocking reagent (from the M.O.M. kit) or 10% goat serum. Then the tissue sections were incubated with mouse PCNA antibody (1:100) (Cat #M0879, mouse monoclonal Ab, Dako, Carpinteria, Calif.), p16 antibody (1:200) (Cat #sc-1661, mouse monoclonal Ab, Santa Cruz, Santa Cruz, Calif.), or mouse Cox-2 antibody (1:100) (Cat#160126, rabbit polyclonal Ab, Cayman Chemical, Ann Arbor, Mich.), respectively, for 60 min at room temperature. The sections were incubated with secondary antibodies (1:200, anti-mouse IgG from the M.O.M kit for p16; ready to use anti-rabbit IgG from the Invitrogen SuperPicture kit for Cox-2; and ready to use anti-mouse IgG from the Dako Envision™ HRP (DAB+) kit for mouse PCNA). As a negative control, sections were stained without incubation with primary antibodies. Finally, signals were visualized based on a peroxidase detection mechanism with 3,3-diaminobenzidine (DAB) (Zymed SuperPicture kit, Invitrogen Corp., Carlsbad Calif.) used as the substrate. The cells with distinct nuclear staining were regarded as positive for PCNA and p16. Four to five representative areas of each mouse tongue section were photographed and analyzed.

Statistical analysis of the data. The statistical analysis of the results was carried out using a one-way analysis of variance test followed by a Bonferroni's multiple comparison test, Fisher's exact probability test, and Wilcoxon rank sum test for multiple comparisons. Differences with a $p<0.05$ were considered statistically significant.

Example 2. D-Arg-2',6'-Dmt-Lys-Phe-NH$_2$ Reduced the Multiplicity and Severity of Mouse Tongue Tumors Induced by 4-NQO All of the mice survived the 10 week 4-NQO treatment, and the subsequent 15 week post-4-NQO period (FIG. 1A). No obvious tongue lesions were observed in all mice at the termination of 4-NQO treatment, consistent with previous findings. See Tang et al., *Clin Cancer Res.*, 10(1):301-13 (2004); Tang et al., *Cancer Biol. & Ther.*, 8(13): 1212-1213 (2009); Tang et al., *Cancer Prev Res.*, 2(12):1100-10 (2009); Osei-Sarfo et al., *Carcinogenesis* (2013), doi: 10.1093/carcin/bgt223. PubMed PMID: 23784083.

Figure 1B:
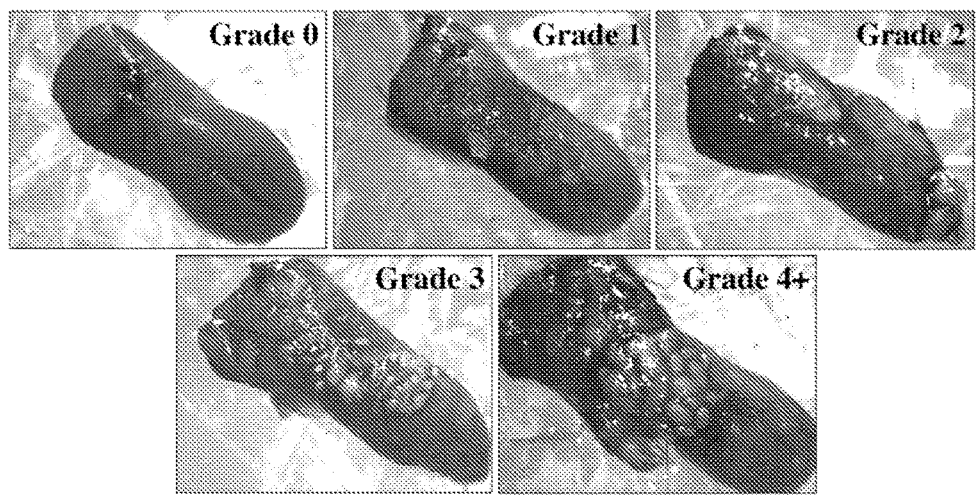
Figure 2A:
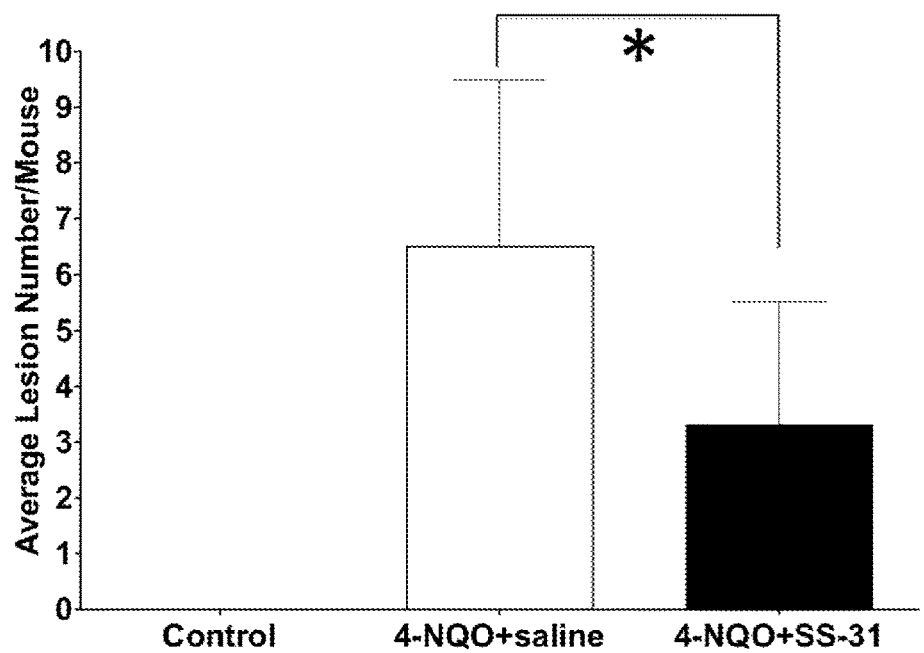
FIG. 2A shows the multiplicity, i.e. number of cancerous tongue lesions per mouse in each treatment group. A one way ANOVA test was used to analyze the differences in tongue lesion numbers among all treatment groups. Differences with a p value of <0.05 (marked with an asterisk) between 4-NQO+saline and 4-NQO+D-Arg-2',6'-Dmt-Lys-Phe-NH$_2$ groups were considered to be statistically significant.
Figure 2B:
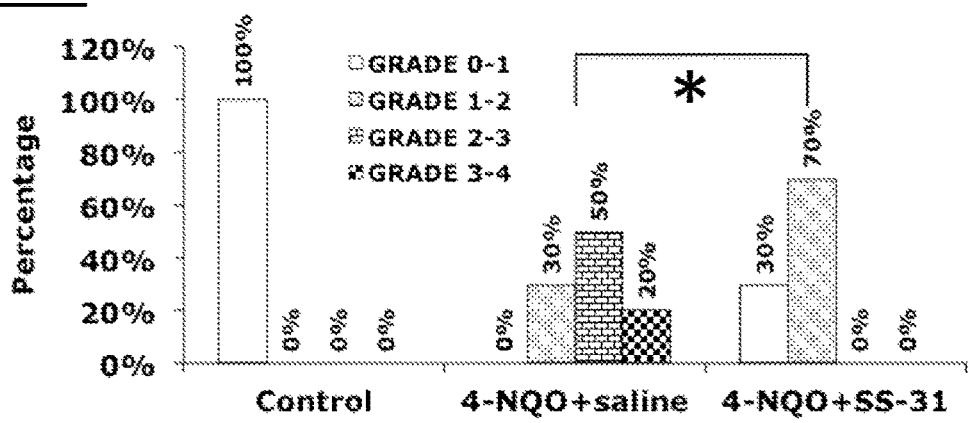
FIG. 2B shows the severity of the cancerous tongue lesions in each treatment group. The differences among the distributions of lesions of different grades in each treatment group were analyzed using a Fisher's Exact probability test. Differences with a p value of <0.05 between the 4-NQO+saline group and the 4-NQO+D-Arg-2',6'-Dmt-Lys-Phe-NH$_2$ group were considered statistically significant (indicated by an asterisk).

However, 4-NQO treated mice developed multifocal, precancerous and cancerous lesions (papillomas, squamous cell carcinomas) during the 15 week post-4-NQO treatment period, and these lesions were primarily located on the dorsal side of the tongue. In contrast, no tongue lesions (Grade 0) were detected in control mice that were not treated with 4-NQO (FIG. 1B). The gross multiplicity of tongue lesions (numbers of lesions of tongues) was determined. Mice in the 4-NQO plus saline (4-NQO+saline) treatment group displayed multiple cancerous tongue lesions of various sizes, and the average number of lesions was 6.5±2.9. Mice in 4-NQO+D-Arg-2',6'-Dmt-Lys-Phe-NH$_2$ group showed a lower average lesion number of 3.3±2.2 (FIG. 2A) ($p<0.05$). Additionally, mice in the 4-NQO+saline group developed severe tongue lesions; 70% of the tongues in this group showed lesions more severe than grade 2, and no mice developed tongue lesions of grades 0-1 (FIG. 2B). In contrast, D-Arg-2',6'-Dmt-Lys-Phe-NH$_2$ treatment resulted in a greater percentage (100%) of less severe tongue lesions of grades 0-2 (FIG. 2B). Statistical analyses with Fisher's exact probability test showed a statistically significant difference in tongue lesion grades between the 4-NQO+saline group and the 4-NQO+D-Arg-2',6'-Dmt-Lys-Phe-NH$_2$ group ($p<0.05$).

Figure 3A:
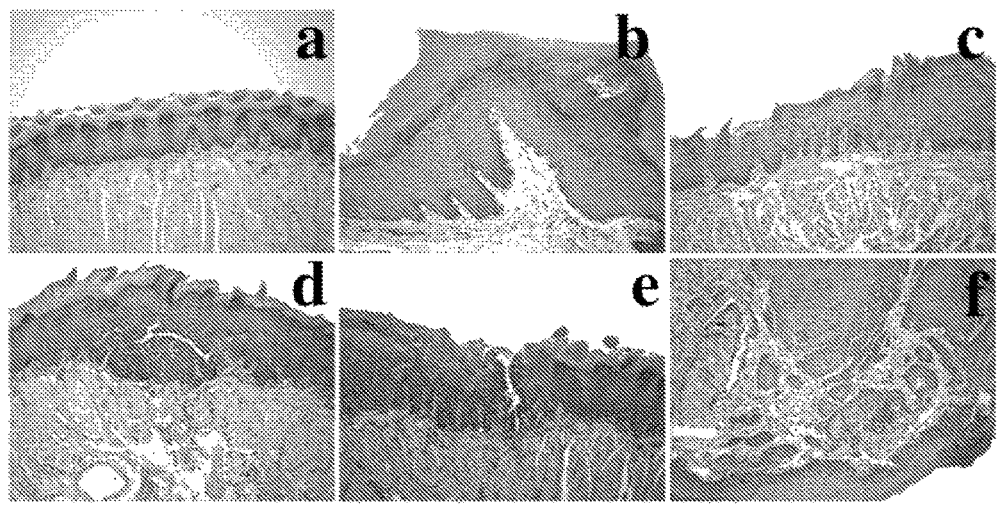
FIG. 3A shows representative images of the different stages of oral carcinogenesis in mouse tongues as indicated by hematoxylin and eosin (H&E) staining: (a) control tongue; (b) hyperplasia with marked hyperkeratosis; (c) mild dysplasia; (d) moderate dysplasia; (e) severe dysplasia/carcinoma in situ; and (f) invasive carcinoma with tumor cells invading the skeletal muscle fibers of the tongue.
Figure 3B:
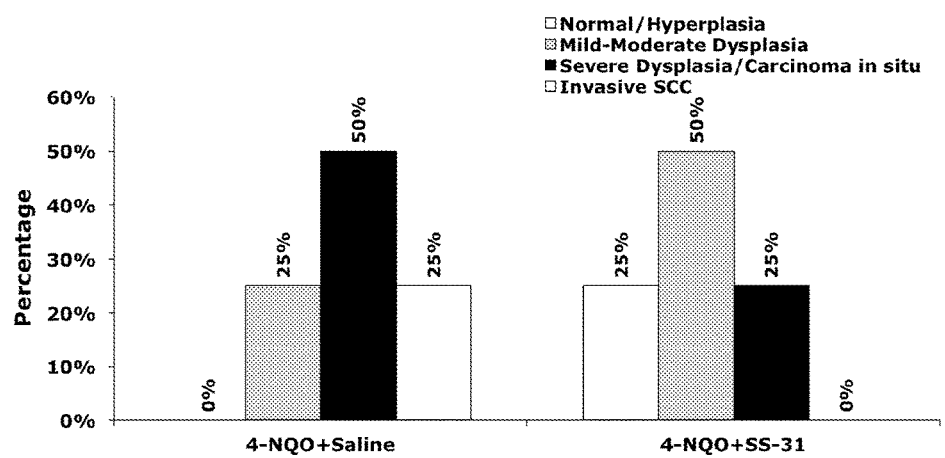
FIG. 3B shows the percentage of 4-NQO treated mouse tongue samples in each treatment group at different stages of carcinogenesis. Mouse tongues were fixed, embedded in paraffin, and sectioned into 5 μm sections. The histological diagnosis of squamous neoplasia (four representative mice per group, based on the lesion grades) was performed on the H&E stained tissue samples.

Pathological analyses on the tongue sections from 4-NQO treated mice were performed. As shown in the representative pictures (FIG. 3A), the mouse tongue sections displayed different stages of oral carcinogenesis, including hyperplasia, dysplasia (mild, moderate, and severe), and carcinoma (including carcinoma in situ and invasive carcinoma). Some samples contained multiple cancerous lesions at different stages. In the 4-NQO+saline group, 75% of the mice had developed severe dysplasia, carcinoma in situ, and invasive carcinoma (FIG. 3B). In contrast, only 25% of the mice in the 4-NQO+D-Arg-2',6'-Dmt-Lys-Phe-NH$_2$ group developed lesions at these severe stages, a percentage much lower than that of the 4-NQO+saline group (FIG. 3B) ($p=0.07$).

These results demonstrate that the aromatic-cationic peptides of the present technology are useful in reducing the multiplicity and severity of oral tumors in subjects suffering from oral carcinogenesis.

Figure 4A:
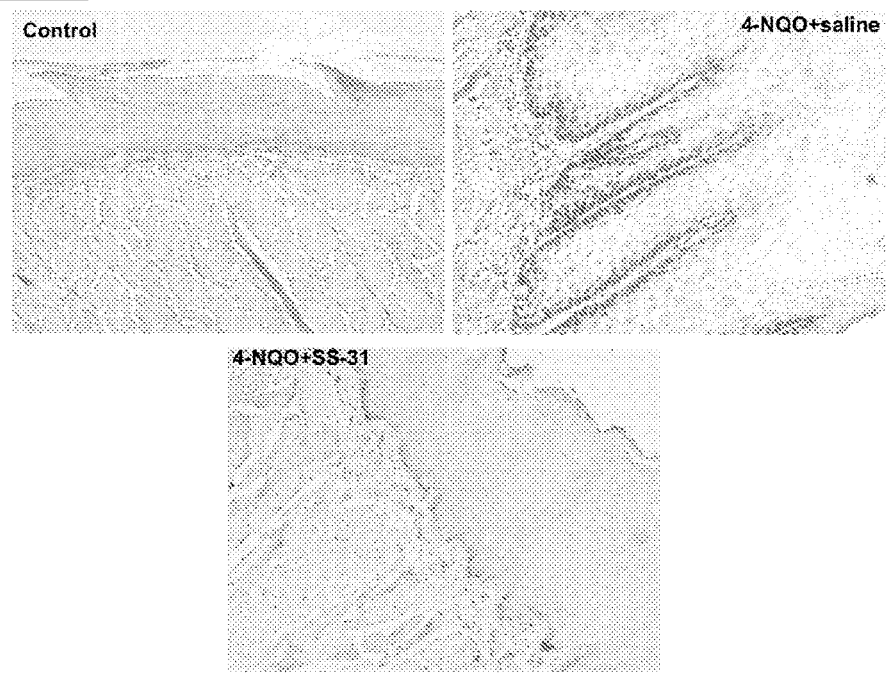
FIGS. 4A-B show PCNA protein levels in mouse tongues for each treatment group. Mice were sacrificed, and the tongues were fixed, embedded, sectioned, and stained with an antibody against PCNA (four mice per group, 300×). Four or five representative areas of each mouse tongue section (2 sections/mouse) were photographed and analyzed.
Figure 4B:
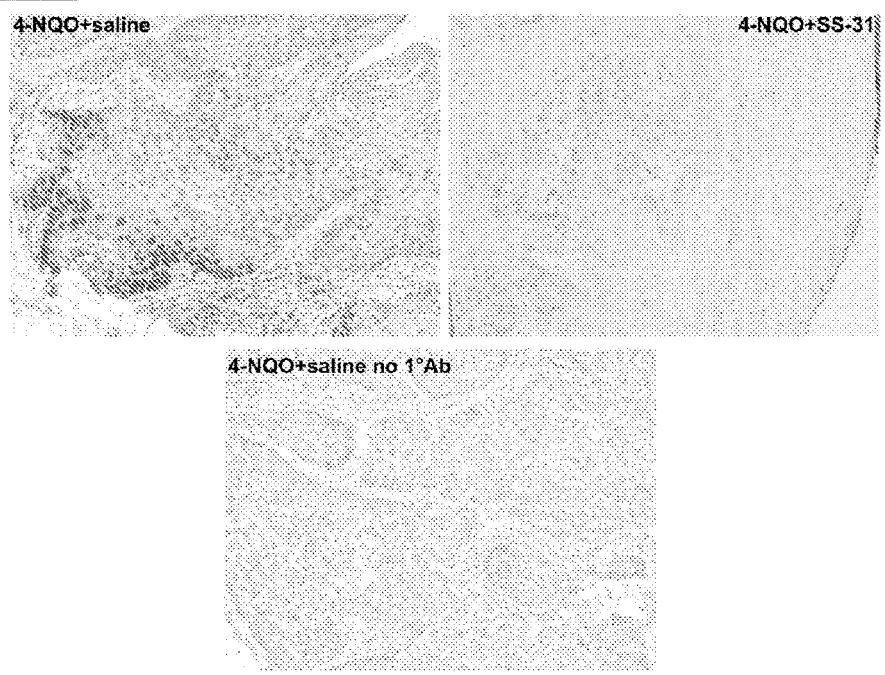

Example 3. Effects of D-Arg-2',6'-Dmt-Lys-Phe-NH$_2$ on PCNA, p16, and Prostaglandin-Endoperoxide Synthase 2 (PTGS2) Protein Levels in Mouse Tongues Proteins involved in oral carcinogenesis in both human and mouse, such as PCNA, p16, and prostaglandin-endoperoxide synthase 2 (PTGS2) were examined. Proliferating cell nuclear antigen (PCNA) is a nuclear protein and is required during the S phase of the cell cycle because it is needed for DNA polymerase delta to bind DNA. Therefore, PCNA is a marker of cell proliferation. Immunohistochemistry showed very few nuclei in the tongue epithelia from the control mice (non-4-NQO treated) that were PCNA positive, whereas treatment with 4-NQO resulted in a large increase in the PCNA positive nuclei in both the tongue epithelial regions without visible lesions and the regions with visible lesions (FIGS. 4 A and 4B). Further, the 4-NQO+D-Arg-2', 6'-Dmt-Lys-Phe-NH2 treatment group showed obvious lower numbers of PCNA positive cells than in the 4-NQO+ saline group (FIGS. 4A and 4B).

These results demonstrate that the aromatic-cationic peptides of the present technology are useful in reducing the expression of PCNA in subjects suffering from oral carcinogenesis.

Figure 5:
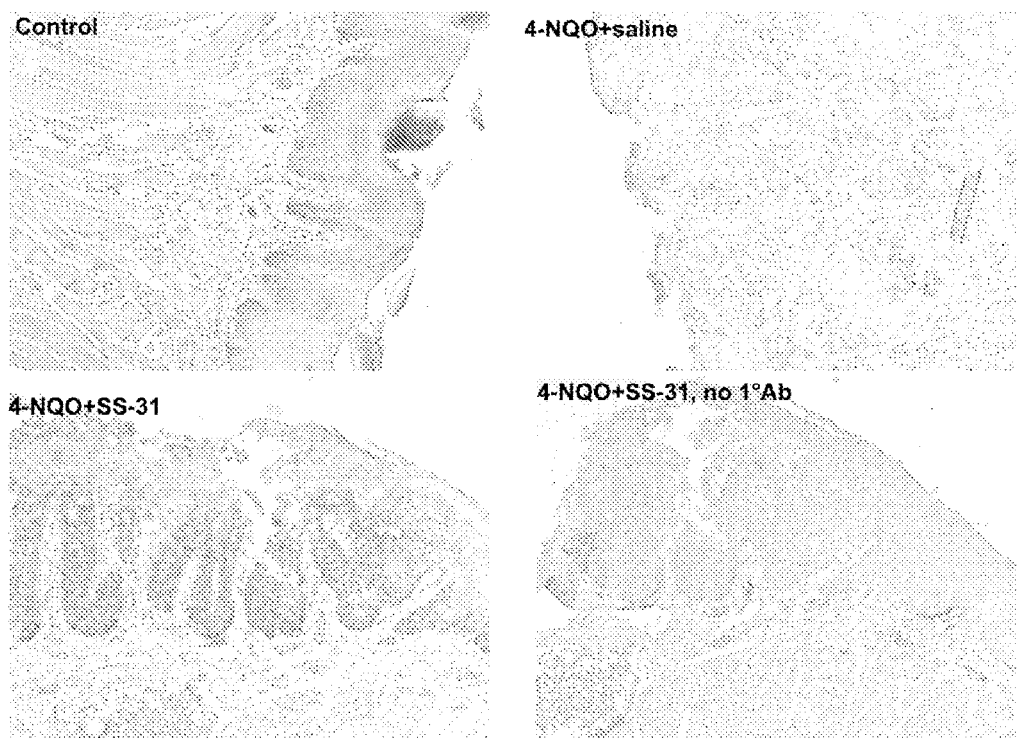
FIG. 5 shows p16 protein levels in mouse tongues for each treatment group. Mice were sacrificed, and the tongues were fixed, embedded, sectioned, and stained with an antibody against p16 (four mice per group, 200×). Four or five representative areas of each tongue section (2 sections/mouse) were photographed and analyzed.

Dysregulation of the cell cycle is common, and critical for the development of cancers. The loss of expression of p16, one of the cell cycle inhibitors, has been observed in oral premalignant lesions and primary tumors of the oral cavity. The protein levels of p16 in the tongues from the control, 4-NQO+saline, and 4-NQO+D-Arg-2',6'-Dmt-Lys-Phe-NH$_2$ treatment groups were compared. In control mouse tongues (non-4-NQO treated) p16 nuclear staining was observed in the epithelial basal and suprabasal layers, but primarily in the basal layer, and 4-NQO treatment resulted in an obvious reduction in p16 protein levels in tongue epithelium (FIG. 5). D-Arg-2',6'-Dmt-Lys-Phe-NH$_2$ injections after 4-NQO treatment greatly limited the 4-NQO-induced decrease in p16 protein levels in tongue epithelium (FIG. 5).

These results demonstrate that the aromatic-cationic peptides of the present technology are useful in restoring the expression of p16 in subjects suffering from oral carcinogenesis. These results also demonstrate that the aromatic-cationic peptides of the present technology are useful in ameliorating or treating cell cycle dysfunction in subjects suffering from oral carcinogenesis. Further, these results demonstrate that the aromatic-cationic peptides of the present technology such as D-Arg-2',6'-Dmt-Lys-Phe-NH$_2$, are also useful in treating or ameliorating other types of cancers, including non-small cell lung carcinoma (NSCLC) and colorectal cancer because p16 silencing is observed in these cancers (See Lou-Qian Z, et al., *PLoS One* 8(1):e54970 (2013); Bihl M P et al., *J Transl Med* 10:173 (2012); Shima K. et al., *Int J Cancer* 128(5):1080-1094 (2011)).

Figure 6:
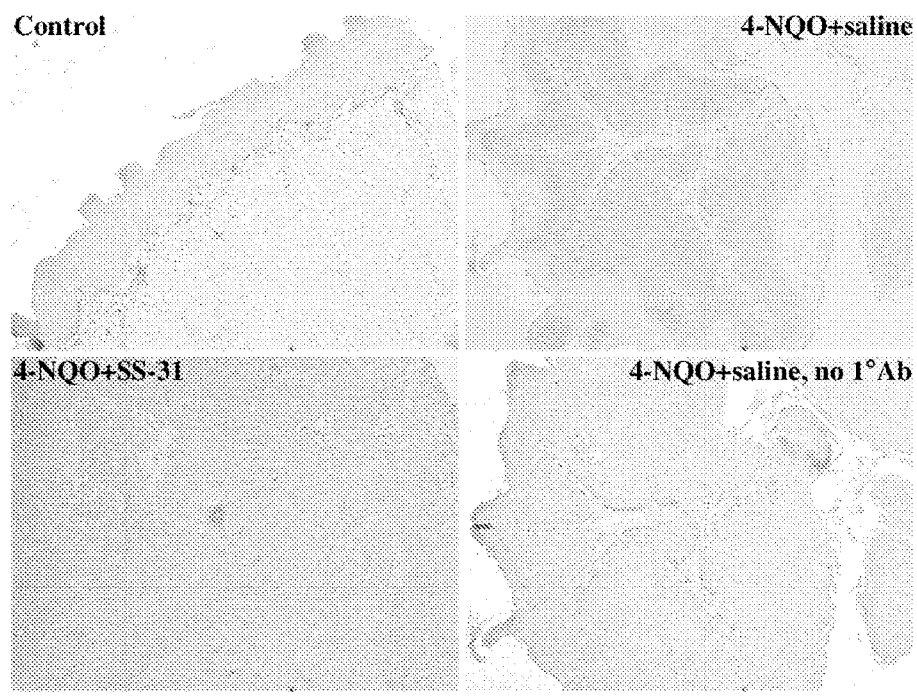
FIG. 6 shows PTGS2 protein levels in mouse tongues for each treatment group. Mice were sacrificed, and the tongues were fixed, embedded, sectioned, and stained with an antibody against PTGS2 (four mice per group, 200×). Four or five representative areas of each tongue section (2 sections/mouse) were photographed and analyzed.

PTGS2 (Prostaglandin-endoperoxide synthase 2, also known as cyclooxygenase-2 or simply COX-2) protein expression in the tongues was investigated because PTGS2 plays an important role in human oral carcinogenesis and increased PTGS2 expression is observed during mouse oral carcinogenesis. PTGS2 staining was not detected in control (non-4-NQO treated) mouse tongue epithelium, but an increase in PTGS2 protein levels was observed in the 4-NQO-induced tongue lesions (FIG. 6). The tongues from the 4-NQO+D-Arg-2',6'-Dmt-Lys-Phe-NH$_2$ group displayed greatly reduced levels in PTGS2 protein (FIG. 6).

These results demonstrate that the aromatic-cationic peptides of the present technology are useful in reducing the expression of PTGS2 in subjects suffering from oral carcinogenesis. Further, these results demonstrate that the aromatic-cationic peptides of the present technology are also useful in treating or ameliorating colon, breast, prostate and lung cancers because PTGS2/Cox-2 overexpression is observed in these cancers (See Harris R E, *Inflammapharmacology* 17(2):55-67 (2009)).

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that the present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method of treating oral cancer in a subject in need thereof comprising administering to the subject a therapeutically effective amount of an aromatic-cationic peptide or a pharmaceutically acceptable salt thereof.

2. The method of claim 1, wherein the oral cancer is a squamous cell carcinoma.

3. The method of claim 1, wherein the aromatic-cationic peptide is D-Arg-2',6'-Dmt-Lys-Phe-NH$_2$ or Phe-D-Arg-Phe-Lys-NH$_2$.

4. The method of claim 1, wherein the subject displays elevated levels of one or more of proliferating cell nuclear antigen (PCNA), p16, and Prostaglandin-endoperoxide synthase 2 (PTGS2) compared to a healthy normal control.

5. The method of claim 1, wherein administration of the aromatic-cationic peptide results in a reduction in the number of oral tumors.

6. The method of claim 1, wherein administration of the aromatic-cationic peptide results in a decrease in the severity of oral tumors.

7. The method of claim 1, wherein the aromatic-cationic peptide is administered orally, topically, intranasally, systemically, locally intramuscularly, intravenously, subcutaneously, intracerebroventricularly, intrathecally, transdermally or with iontophoresis.

8. The method of claim 1, wherein the subject is human.

9. The method of claim 1, wherein the oral cancer comprises one or more of leukoplakia (white lesions), erythroplakia, lumps or thickening in the oral soft tissues, soreness, difficulty chewing, speaking or swallowing, ear pain, difficulty moving the jaw or tongue, hoarseness, numbness of the tongue or other areas of the mouth, oral bleeding, wart-like masses and swelling of the jaw that changes the way teeth or dentures fit together.

10. The method of claim 1, wherein the pharmaceutically acceptable salt comprises acetate or trifluoroacetate salt.

11. The method of claim 1, wherein the aromatic-cationic peptide is administered at regular intervals over a period of one, two or several months.

12. The method of claim 1, wherein the regular intervals are every day, every other day, every 3 days, every 4 days, every 5 days, every 6 days or once a week.

* * * * *